United States Patent [19]

Jinotti

[11] 4,014,010

[45] Mar. 22, 1977

[54] FLUID-DISPENSING APPARATUS HAVING LEVEL CONTROL AND ALARM MEANS

[76] Inventor: Walter Joseph Jinotti, 10 Scott St., New Brunswick, N.J. 08901

[22] Filed: Aug. 1, 1975

[21] Appl. No.: 601,147

[52] U.S. Cl. .................. 340/244 A; 128/214 C; 128/214 E; 340/239 R

[51] Int. Cl.² ........................................ G08B 21/00

[58] Field of Search .............. 340/244 A, 239 R; 128/214 C, 214 E, 214 F, DIG. 12, DIG. 13

[56] References Cited

UNITED STATES PATENTS

| | | | |
|---|---|---|---|
| 352,647 | 11/1886 | Ghegan | 340/244 A |
| 3,003,500 | 10/1961 | Barton et al. | 128/214 F |
| 3,150,360 | 9/1964 | Stenzel | 340/239 R |
| 3,543,752 | 12/1970 | Hesse et al. | 128/214 E |
| 3,689,908 | 9/1972 | Ray | 340/239 R |

FOREIGN PATENTS OR APPLICATIONS 2,202,402  1/1972  Germany ............... 128/214 E

*Primary Examiner*—Donald J. Yusko
*Assistant Examiner*—Daniel Myer
*Attorney, Agent, or Firm*—Robert A. Green

[57] ABSTRACT

The apparatus comprises a flexible tube through which fluid flows from a supply, and a opaque ball which is adjustably disposed within the tube. When fluid is first fed through the tube, an air bubble forms, and the location of this bubble is set by squeezng the tube and forcing the air bubble to an upper portion of the tube. The opaque ball rests on the top surface of the fluid in the air bubble. A photoelectric detector assembly comprising a source of light and a light detector is mounted on the tube, with the beam of light interrupted by the opaque ball. The light detector is connected to an electronic circuit which is arranged to perform no function so long as the beam of light from the source is interrupted by the ball. When all of the fluid has been fed through the tube from the source, and the level begins to drop in the tube, the opaque ball drops below the light beam and permits the light detector to receive light from the light source, and the resultant current flow operates the electronic circuit to provide a warning that the fluid has dropped below the set level and that the tube itself will be empty in a known period of time thereafter.

6 Claims, 1 Drawing Figure

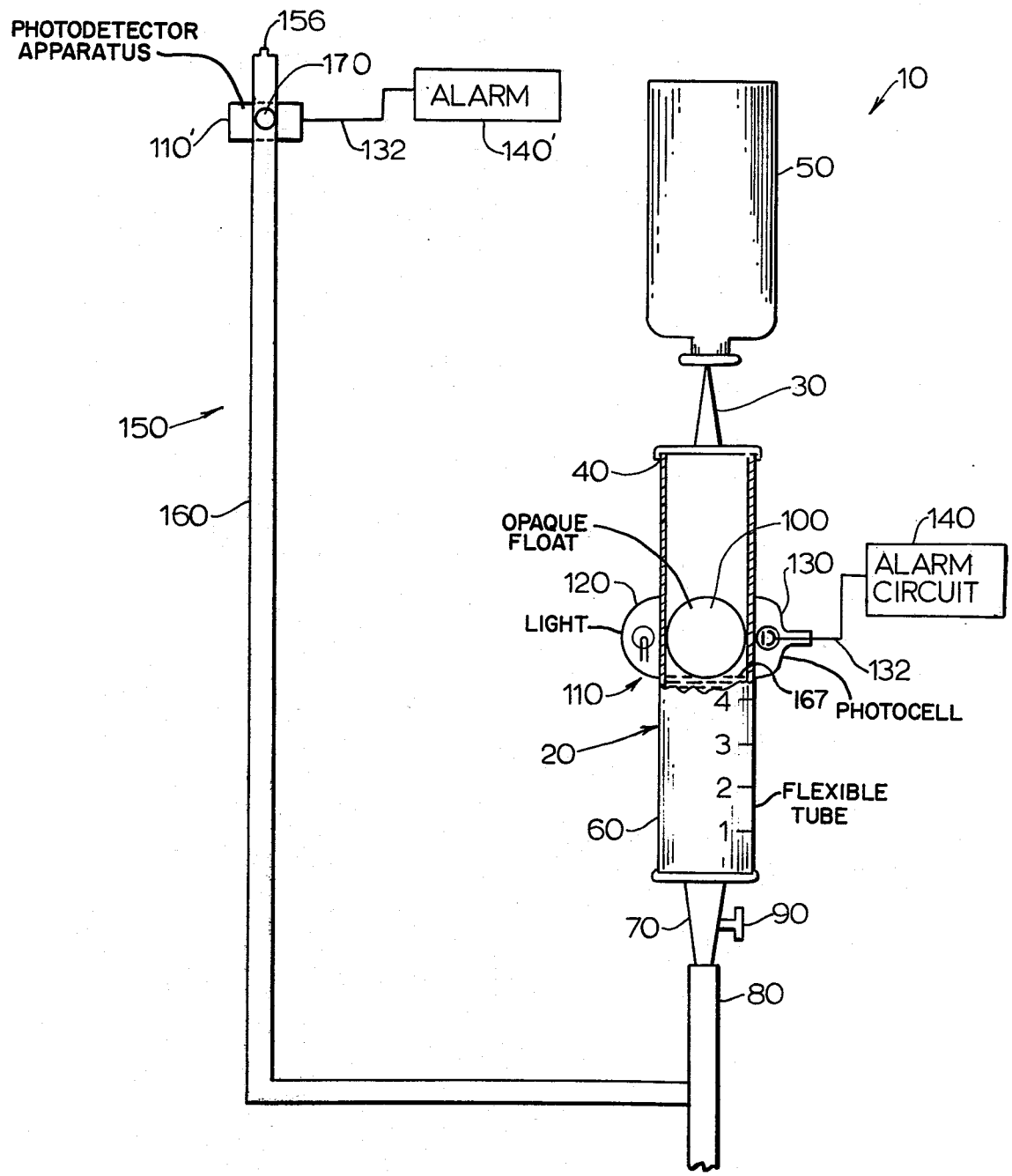

FLUID-DISPENSING APPARATUS HAVING LEVEL CONTROL AND ALARM MEANS

BACKGROUND OF THE INVENTION

Fluid flow control apparatus is well known in the art. Generally, apparatus of this type either counts drops of fluid which is dispensed, or it is arranged to respond when the fluid source is empty. None of the prior art apparatus has the advantage of the present invention in which the alarm fluid level can be readily adjusted and detected, and in which the period of time following such detection in which some fluid is still available is controllable. In a medical application, this available time period permits a nurse to respond to the alarm and to replace the fluid supply.

SUMMARY OF THE INVENTION

Briefly, the invention comprises a tube which is placed in the fluid flow line and in which the fluid alarm level can be adjusted as desired, and a photoelectric detector is provided for sensing this alarm level.

DESCRIPTION OF THE DRAWINGS

The single FIGURE is an elevational view, partly in section, of apparatus embodying the invention.

DESCRIPTION OF THE PREFERRED EMBODIMENTS

The present invention is particularly useful in medical applications for feeding intravenous fluid, blood, or the like, from a bottle to a patient and providing an alarm when the fluid is almost depleted and has only a few minutes to run. The principles of the invention; however, are useful in other areas, and such other uses will be apparent to those skilled in the art.

Apparatus 10 embodying the invention includes a tube 20 made of a transparent synthetic resinous material and having a flexible wall which can be squeezed by finger pressure but which returns to its original shape when the pressure is removed. The tube 20 has an inlet fixture 30 at its upper end 40 which can be connected directly or through suitable tubing to a bottle 50 of fluid, and its other end 60 carries a similar fixture 70 which can be connected to a feed tube 80 which is adapted to be inserted into a patient's arm or the like. A suitable valve means 90 is provided in fixture 70 or in tubing 80 to control fluid flow. The two fixtures 30 and 70 may be in a form which permits them to be removably secured to the upper and lower ends of the tube 20.

An opaque ball 100 is disposed within the tube 20, and the tube may carry markings representing minutes' worth of fluid present in the tube. Thus, if the fluid level is at marker 1, then this quantity of fluid will flow out of the tube in one minute, and, similarly, the other markings represent the time required to dispense fluid present at that level.

The apparatus of the invention also includes a photodetector assembly 110 which is adapted to be clamped to the tube and includes a source of light 120 and a photocell 130, with the photocell being coupled by lead 132 to an electronic alarm circuit 140. The alarm circuit 140 may be of any suitable type and may provide an audible alarm itself, or it may transmit a radio signal to a remote alarm at a remote nurse's station.

In operation of the invention, with the photodetector apparatus 110 removed from the tube 20 and with valve 90 closed, fluid is permitted to flow from the bottle 50 and through fixture or tube 30 into deformable tube 20. Only a small quantity of fluid can flow into tube 20, and this flows to the bottom of tube 20 and air fills the rest of the tube. The tube 20 is then squeezed to force air back into the bottle 50, and, at the same time, fluid flows from the bottle into the tube. This operation is performed until sufficient fluid enters tube 20 to raise ball 100 to a desired height, and this provides, beneath the ball, a quantity of fluid 167 which will flow out of the tube in a predetermined length of time. With the ball positioned as desired, the photodetector assembly 110 is clamped to the tube 20, with the ball 110 interrupting the beam of light so that the light does not strike the photocell 130. Fluid is now permitted to flow in the system, and, when the source 50 is empty and the remaining fluid begins to flow out of the tube 20, the level of fluid in the tube begins to drop, the opaque ball 100 drops below the level of the photocell and permits light to strike the photocell. This causes current flow which operates the alarm circuit 140. This warns a nurse that the preset quantity of fluid remains in the tube, and she can take the necessary corrective action.

As an optional adjunct to the basic apparatus described above, to monitor the pressure against which fluid is dispensed, a generally L-shaped side tube 150 is connected to outlet member 70 or tube 80 and includes a vertical tube 160 which extends upwardly adjacent to the fluid source 50 to an open end 156. An opaque ball 170 is provided within the tube 160 along with a photoelectric detector 110', like detector 110, for sensing fluid level and the position of the opaque ball 170. In operation of this apparatus when fluid is being dispensed, a level of fluid will appear in the vertical side tube 160 representing normal flow. The ball 170 and photosensitive apparatus 110' is set at this level. If the pressure against which fluid is dispensed increases, a condition to be detected, the level of fluid in the tube 160 will rise and raise the opaque ball out of operative relation with the photosensitive apparatus which will then operate to energize alarm 140'.

What is claimed is:

1. Liquid level sensing and alarm apparatus comprising a container of fluid to be dispensed disposed generally vertically and having an outlet, through which fluid can flow, a deformable tube disposed generally vertically and having an inlet at its upper end and an outlet at its lower end, said inlet at said upper end of said tube being coupled directly, and in open communication, to said outlet of said container, an outlet pipe connected to said outlet of said tube and having valve means for opening and closing said outlet pipe to fluid flow from said tube and said container, said tube having indicia display means denoting different final quantities of fluid therein and different times for dispensing such different final quantities of fluids therefrom, an opaque float present in said tube and positionable at different levels therein depending on the quantity of fluid present therein, first photoelectric detector means coupled to said tube and adjustably positionable at the level of said opaque float member and thus settable to detect the upper level of a quantity of fluid therein, a second side tube connected to said outlet pipe and having a vertical tube portion in which fluid is present when fluid is flowing from said container, a second opaque float in said second tube through which light will not pass, and second photoelectric detector means in operative relation with said second tube and said second opaque float for sensing a change in an established liquid level in said second tube, said deformable tube being deformable so that, with said valve closed, air can be squeezed out of said tube into said container of fluid and then a selected quantity of fluid can flow into said tube from said container to a desired level beneath said opaque member, said desired level representing one of said different final quantities of fluid and representing to an operator of the apparatus, the last quantity of fluid to be dispensed from the tube and the time period for said last quantity of the fluid to be dispensed, said first photoelectric detector means including means for providing an alarm when said last quantity of fluid begins to be dispensed from said tube.

2. The apparatus defined in claim 1 wherein said indicia display means associated with said tube comprises calibration markings in its wall, each marking denoting a different quantity of fluid and dispensing time therefor.

3. The apparatus defined in claim 1 wherein said opaque float is a ball which is supported by fluid in said tube.

4. The apparatus defined in claim 1 wherein said photoelectric detector means is a source of light and a photocell positioned to receive said light.

5. The apparatus defined in claim 1 wherein said second opaque float is a ball which is supported by fluid in said second tube.

6. The apparatus defined in claim 1 and including an alarm means coupled to said photoelectric detector means and responsive to changes in fluid level in said second tube detected by said photoelectric detector means.

* * * * *